United States Patent [19]

Hotchkiss, Jr. et al.

[11] Patent Number: 5,056,523
[45] Date of Patent: Oct. 15, 1991

[54] PRECISION BREAST LESION LOCALIZER

[75] Inventors: John E. Hotchkiss, Jr., Tiburon, Calif.; Granville C. Coggs, San Antonio, Tex.

[73] Assignee: Board of Regents, The University of Texas System, Austin, Tex.

[21] Appl. No.: 441,114

[22] Filed: Nov. 22, 1989

[51] Int. Cl.⁵ .............................................. A61B 5/00
[52] U.S. Cl. ............................... 128/653 R; 606/130; 378/37
[58] Field of Search ............ 128/653 R, 749, 751–754; 606/130; 378/20, 37, 177, 179, 180, 195, 196; 269/322, 328

[56] References Cited

U.S. PATENT DOCUMENTS

| | | | |
|---|---|---|---|
| 3,508,552 | 4/1970 | Hainault | 606/130 |
| 3,817,249 | 6/1974 | Nicholson | 606/130 |
| 4,427,005 | 1/1984 | Tener | 606/130 |
| 4,580,561 | 4/1986 | Williamson | 606/130 |
| 4,599,738 | 7/1986 | Paretta et al. | 378/37 |
| 4,691,333 | 9/1987 | Gabriele et al. | 128/754 |
| 4,784,134 | 11/1988 | Arana | 128/749 |
| 4,821,727 | 4/1989 | Levene et al. | 128/653 R |
| 4,875,478 | 10/1989 | Clen | 606/130 |

OTHER PUBLICATIONS

Denarnaud et al., "Stereotactic Breast Puncture: New Step in Breast Screening", Diagnostic Imaging, pp. 189–191, (Oct. 1987).
Gent, H. J. et al., "Stereotaxic Needle Localization and Cytological Diagnosis of Occult Breast Lesions," Annals of Surgery, 204(5), 580–583, (Nov. 1986).
Bottles et al., "Fine-Needle Aspiration Biopsy, Has Its Time Come!", The American Journal of Medicine, vol. 81, pp. 525–531, (Sep. 1986).
Smith, C. et al., "Fine-Needle Aspiration Cytology in the Diagnosis of Primary Breast Cancer", Surgery, vol. 103, No. 2, pp. 178–183, (Feb. 1988).
Bibbo, M. et al., "Stereotaxic Fine-Needle Aspiration Cytology of Chemically Occult Malignant and Pre-Malignant Breast Lesions", ACTA Cytol, 32(2):193–201, (Mar.-Apr. 1968).
Dowlatshahi, K. et al., "cytologic Diagnosis of Occult Breast Lesions Using Stereotaxic Needle Aspiration. A Preliminary Report," Arch Surg., 122(11):1343–1346, (Nov. 1987).
Hall, W. C. et al., "Evaluation of Nonpalpable Breast Lesions", American Journal of Surgery, 151:467–469, (Apr. 1986).
Bolmgren et al., "Stereotaxic Instrument for Needle Biopsy of the Mamma", (Jul. 1, 1989).
Azavedo et al., The Lancet-Saturday, May 13, 1989 to Coggs, 75th Scientific Assembly and Meeting, (May 1989).

(List continued on next page.)

Primary Examiner—Ruth S. Smith
Attorney, Agent, or Firm—Arnold, White & Durkee

[57] ABSTRACT

A device and method for precisely positioning a probe tip relative to a target lesion in a bodily protuberance is provided. The protuberance to be probed is secured between a first and a second radiolucent platform. The platforms are in parallel and spaced relation and the second platform comprises a plurality of passages for insertion of a probe. Radiopaque markers on the second platform aid in locating the lesion in a radiograph of the target taken along a first path through the second platform, target and first platform. Utilizing the radiograph, a probe guide comprising a plurality of passages is positioned immediate the lesion to enable the positioning of a probe coincident the lesion along the first path. A radiopaque scale is positioned coplanar the probe guide to indicate distance along the first path enabling the creation of a second radiograph indicating the depth of the lesion relative to the probe guide and the radiopaque scale. This scale allows calculation of the depth of the lesion and enables a needle to be precisely inserted to the point of the lesion. Cells of the lesion may then be aspirated through the needle for examinaiton. Where the bodily protuberance is a breast, the substantial surgical procedure involved in a conventional biopsy may be avoided through use of this device and method.

20 Claims, 4 Drawing Sheets

OTHER PUBLICATIONS

Dowlatshahi et al., "Nonpalpable Breast Tumors: Diagnosis with Stereotaxic Localization and Fine-Needle Aspiration," Radiology, (Feb. 1989).

Ciatto et al., "Nonpalpable Breast Lesions: Stereotaxic Fine-Needle Aspiration Cytology," Radiology, vol. 173, No. 1, 57–59, (Oct. 1989).

Kopans, "Fine-Needle Aspiration of Clinically Occult Breast Lesions", Radiology, (Feb. 1989).

Kopans, D. et al., "Preoperative Imaging-Guided Needle Placement and Localization of Clinically Occult Breast Lesions", AJR 152:1–9, (Jan. 1989).

Christopher, R. B. et al., "Stereotactic Guidance for Breast Biopsy Localization and Aspiration", presented as a Scientific Exhibit, Annual Meeting, Radiological Society of America, (Nov. 26–Dec. 1, 1989).

Smit Rontgen, "Breast Biopsy Guide", technical Exhibit Brochure (1986).

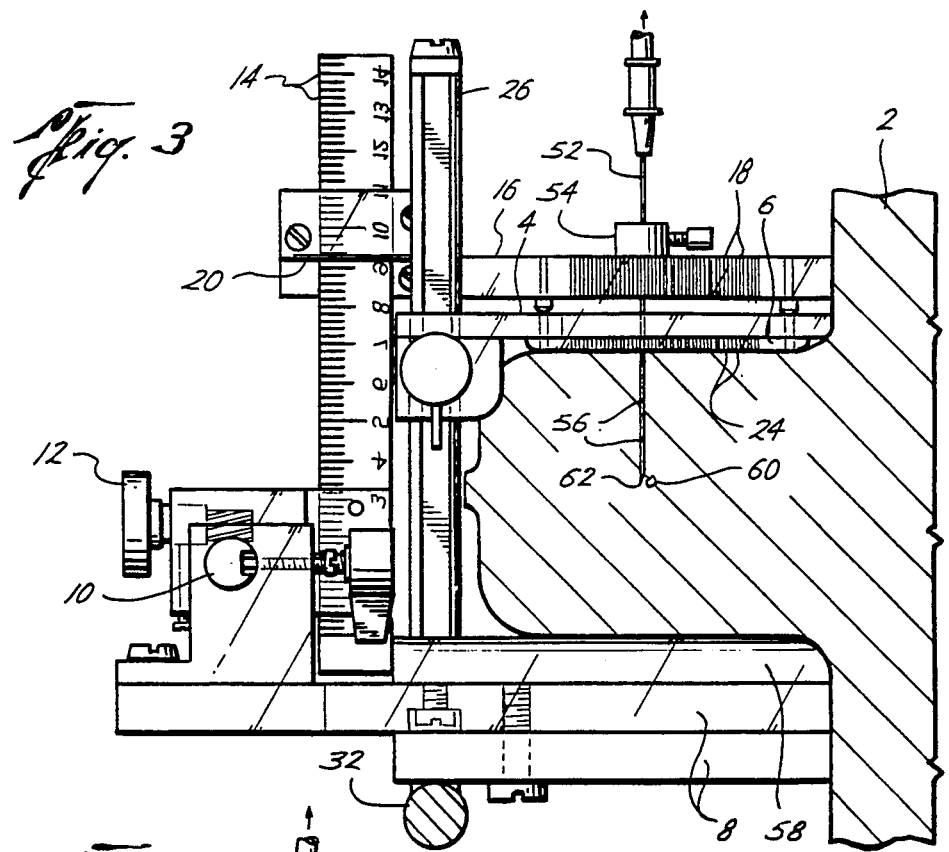
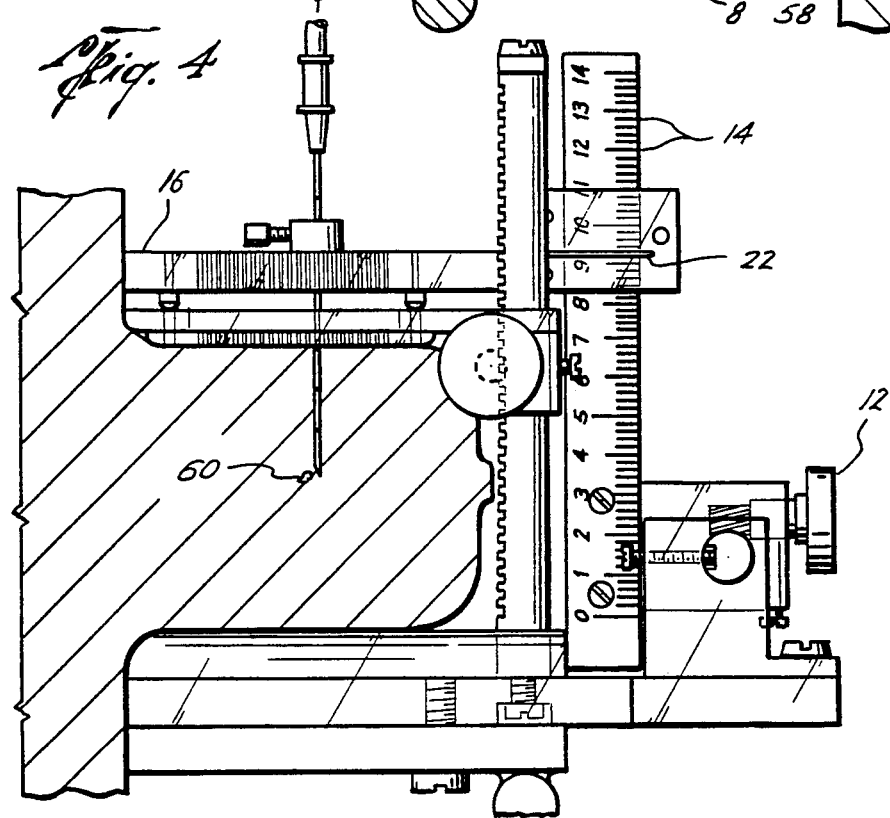

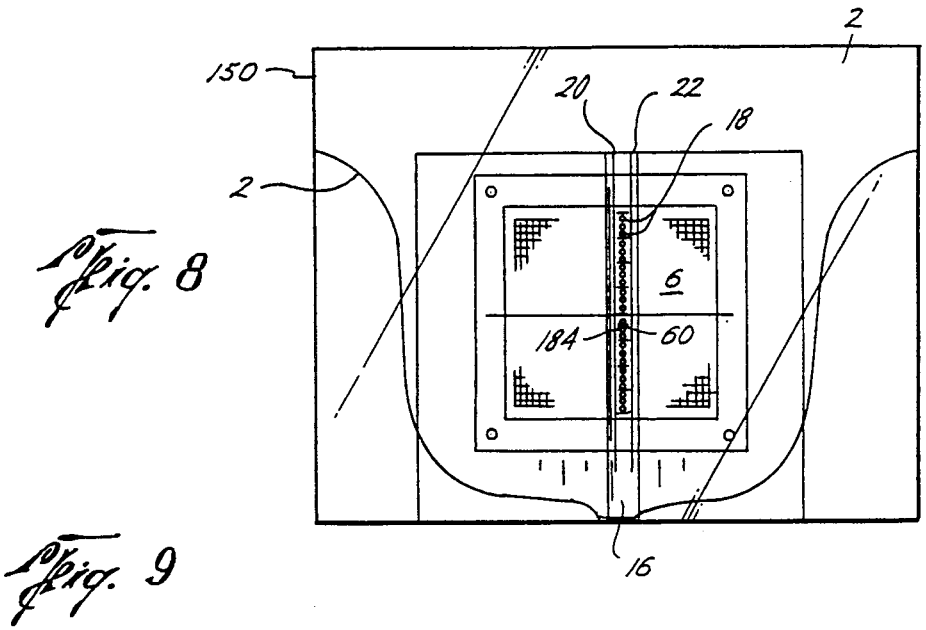
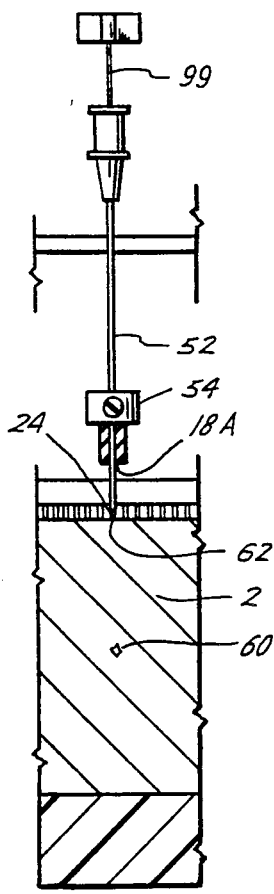
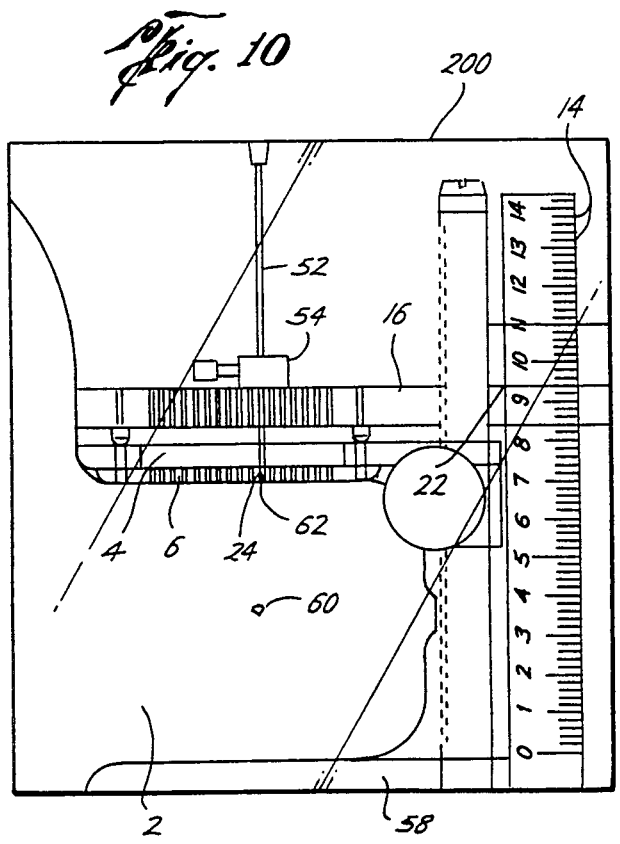

PRECISION BREAST LESION LOCALIZER

BACKGROUND OF THE INVENTION

I. Field of the Invention

This invention relates to a device and a method for accurately positioning a probe in a bodily protuberance relative to a target located in the protuberance. In particular, the invention relates to securing the protuberance and positioning a probe tip proximate the target within the protuberance through the use of radiographs and certain radiopaque markers where the markers are, in part, positioned coplanar to the target and appear in the radiographs.

II. Description of Related Art

The detection of lesions in bodily protuberances, such as the breasts, has been aided in recent years through the use of mammography. One commonly used method of confirming breast cancers related to lesions targeted from a mammogram involves sampling suspect tissue from the target lesion through a biopsy procedure.

The biopsy procedure typically involves positioning a barbed guide wire in the vicinity of or directly in the targeted lesion. A surgeon then follows the wire through the breast tissue to the suspect lesion. The surgeon removes the suspect tissue and the removed tissue is examined for abnormalities such as cancerous cells.

Approximately only one in five such lesions are cancerous. Thus, significant surgical expertise, time, expense and patient suffering result from the approximate four out of five biopsies that show no cancerous cells.

Recently, a less invasive procedure has been developed using mammography and a needle to aspirate cells of the lesion from the body. The aspirated cells may then be examined using known cytopathologic techniques to determine the presence or non-presence of cancerous cells.

In utilizing the needle aspiration procedure, it is imperative that the needle tip be placed with precision at the targeted lesion to insure that the cells aspirated are the cells of the targeted lesion and not merely cells near the lesion.

Precise location of the needle tip for needle aspiration may be accomplished utilizing a stereotactic instrument having an x-ray tube mounted on a hinged arm positionable at precise angles relative to known coordinates. Such devices while enabling accurate needle tip location, are typically costly and often not readily available.

The device and method of the present invention provide a relatively low cost approach to precision location of a needle tip in a breast or other protuberance relative to a targeted lesion.

SUMMARY OF THE INVENTION

The device of the present invention for positioning a probe tip in a bodily protuberance, such as a breast, comprises a base, a first radiolucent platform attached to the base and a second radiolucent platform attached to the base. The second radiolucent platform being adjustably positionable in parallel and spaced relation to the first platform to secure and compress the protuberance between the first and second platforms. The second platform also comprises a radiolucent guide insert and at least one radiopaque insert marker in fixed position relative to the guide insert. The insert comprises a plurality of probe passages positioned in a plurality of rows. A system for supporting and adjusting the parallel and spaced relation of the second platform relative to the first platform is further provided. The device further comprises a radiolucent probe guide comprising a plurality of probe passages, the probe passages being positioned in a row where the passages in the row are preferably spaced in conformity to the spacing of passages in the rows of passages of the insert. The probe guide is adjustably positionable relative to the insert to enable passage of a probe through at least one of the probe guide passages and through at least one of the insert passages. The probe guide being positioned in proximal relation to the second platform and in distal relation to the first platform. Additionally, a system for supporting the probe guide is provided and at least two radiopaque scale markers are positioned in a plane substantially parallel to the row of probe guide passages in a path substantially perpendicular to the first platform.

Preferably, each row of insert passages has the passages substantially symmetrically spaced relative to at least one other row of insert passages. In a preferred embodiment, the spacing of passages in each row of passages in the insert is substantially equal. Further, the scale markers are preferably positioned substantially coplanar to the row of probe guide passages with the scale markers being fixedly positionable relative to the probe guide support system.

In an alternate preferred embodiment, the scale markers are fixedly positionable relative to the probe guide.

In still another preferred embodiment of the present invention, the scale markers are fixedly positionable relative to the second platform.

Preferably, the scale markers comprise a plurality of substantially uniformly spaced radiopaque markers providing a radiopaque measurement tool.

The probe guide is adjustably positionable coincident with at least one of the rows of passages in the insert. The probe guide further comprises at least one lengthwise positioned radiopaque marker in fixed position relative to the probe guide and the radiopaque marker is further preferably positionable in confronting relation with the scale markers. Further, the lengthwise positioned radiopaque marker is preferably positioned in distal relation to the second platform.

In a preferred embodiment, the guide insert is removable from the second platform.

The probe of the present invention preferably comprises a needle having a plurality of spaced markings along a portion of a length of the needle. Additionally, an adjustable probe stop is preferably provided to secure the probe at a desired depth through the probe guide.

Preferably, the device of the present invention further comprises a support system having a radiolucent support member attachable to the device. The radiolucent support member preferably being connectable to an additional support system. The additional support system being positioned in distal relation to the path defined by the second platform, target and first platform.

Another preferred embodiment of the device of the present invention comprises a support system having radiolucent support straps positionable about a patient in the manner of a brassiere to secure the device of the present invention relative to a breast of the patient where the protuberance to be probed is the breast.

Another preferred embodiment of a device of the present invention comprises a base, a first radiolucent platform attached to the base and a second radiolucent platform attached to the base, the second platform being adjustably positionable in parallel and spaced relation relative to the first platform to secure and compress a bodily protuberance between the first and second platforms, the second platform comprising a bore through the second platform. The second platform further comprises at least one radiopaque marker in fixed position relative to the bore. The device also comprises a system for supporting and adjusting the second platform relative to the first platform. The device further comprises a radiolucent probe guide. The probe guide comprises a plurality of probe passages, the passages being positioned in a row and the probe guide being adjustably positionable relative to the bore to enable passage of a probe through the probe guide and the bore. The probe guide being in proximal relation to the second platform and in distal relation to the first platform. The device further comprises a system for supporting the probe guide and at least two radiopaque scale markers positioned in a path substantially perpendicular to the first platform and in a plane parallel to the row of probe guide passages. Preferably, the scale markers are positioned substantially coplanar to the row of probe guide passages and the scale markers preferably comprise a plurality of uniformly spaced radiopaque markers. The probe guide preferably further comprises at least one lengthwise positioned radiopaque marker in fixed position relative to the guide. Further, the lengthwise positioned radiopaque marker is preferably positioned in distal relation to the second platform.

In still another preferred embodiment, the device of the present invention for positioning a probe in a bodily protuberance comprises a base, a first radiolucent platform attached to the base and a second radiolucent platform attached to the base and being adjustably positionable in parallel and spaced relation relative to the first platform to secure and compress a bodily protuberance between the first and second platforms. The device further comprises at least one passage through the second platform and a system for adjusting the spaced relation of the first and second platforms. The device further comprises a system for positioning a probe through the second platform passage where the probe is substantially coincident a target within the protuberance and the probe is positioned along a first path defined by the second platform passage, the target and the first platform. The device further comprises a system for attaching the probe positioning system to the base and further provides a system for positioning at least two radiopaque scale markers substantially coplanar to the first path. The system for positioning the radiopaque scale markers enables the creation of a radiograph created along a path generally transverse to the first path where the radiograph comprises the target and the radiopaque scale markers enabling precise determination of the location of the target and precise positioning of the probe tip immediate the target in the protuberance.

The method of the present invention of positioning a probe tip proximate a target in a bodily protuberance comprises the steps of securing and compressing the protuberance between a first and second radiolucent platform, the platforms being relatively adjustably positionable in parallel and spaced relation, with the second platform comprising a plurality of probe passages and further comprising at least one radiopaque marker in fixed position relative to the second platform probe passages, then creating a first radiograph by directing an energy beam in a first path through the second platform, through the target and through the first platform and onto a first beam sensitive surface, then interposing a radiolucent probe guide in the first path where the probe guide comprises a plurality of probe passages positioned in a row to enable passage of a probe through the probe guide and the second platform toward the target, the row of probe guide passages preferably being substantially perpendicular to the first path, then positioning a radiopaque pointer in at least one of the probe guide passages, the pointer being substantially parallel the first path and coincident the target along the first path, then creating a second radiograph by directing an energy beam in a second path through the target, through a plurality of radiopaque markers positioned substantially coplanar to the row of probe guide passages where the plurality of markers are positioned to indicate relative distances along the first path, onto a second beam sensitive surface where the second beam path is generally transverse to the first path, then positioning the probe coincident the pointer along the first path and further positioning the probe tip within the protuberance a distance along the first path generally equal to the distance along the first path of the target in the protuberance as indicated by the substantially coplanar positioned plurality of first path markers in the second radiograph.

Preferably, the interposing step further comprises the substep of creating a first-supplemental radiograph by directing an energy beam substantially along the first path through the interposed probe guide, through the second platform, through the target, and through the first platform and onto a first-supplemental beam sensitive surface. Preferably, the probe guide further comprises a lengthwise positioned radiopaque marker in fixed position relative to the probe guide. The first-supplemental radiograph aids in assuring proper positioning of the probe guide.

In a preferred embodiment, the step of creating a second radiograph further comprises the substep of creating a second-supplemental radiograph by directing an energy beam in a third path through the target, through the plurality of radiopaque markers positioned coplanar to the row of probe guide passages and onto a second-supplemental beam sensitive surface. This third path being generally transverse to the first path and the third beam path being generally oppositely directed relative to the second beam path. The second-supplemental radiograph aids in assuring proper positioning of a probe prior to insertion in the protuberance.

The probe positioning step preferably further comprises the substep of positioning the probe tip within the protuberance a distance along the first path substantially equal to the average of the distances along the first path of the target in the protuberance as indicated by the plurality of markers shown in the second and second-supplemental radiographs. Use of average values of the distances enables compensation for potential errors in measurement introduced when the target is not coplanar to the plurality of first path markers.

An alternate preferred method of the present invention for positioning a probe proximate a target in a bodily protuberance comprises the steps of securing and compressing the protuberance between a first and a second radiolucent platform, the platforms being relatively adjustably positionable in parallel and spaced relation where the second platform comprises a bore through the second platform and the second platform further comprises at least one radiopaque marker in fixed position relative to the bore, creating a first radiograph by directing an energy beam in a first path through the second platform, through the target and through the first platform and onto a first beam sensitive surface, interposing a radiolucent probe guide in the first path, the probe guide preferably comprising a plurality of probe passages positioned in a row to enable passage of a probe through the probe guide and through the second platform toward the target where the row of probe guide passages is positioned substantially perpendicular to the first path, positioning a radiopaque pointer in at least one of the probe guide passages, the pointer being substantially parallel the first path and coincident the target along the first path, creating a second radiograph by directing an energy beam in a second path through the target, through a plurality of radiopaque markers positioned coplanar to the row of probe guide passages, the plurality of markers being positioned to indicate relative distances along the first path, and onto a second beam sensitive surface where the second path is generally transverse the first path, positioning the probe coincident the pointer along the first path and further positioning the probe tip within the protuberance a distance along the first path generally equal to the distance along the first path of the target within the protuberance as indicated by the plurality of first path markers in the second radiograph.

The present invention offers significant improvements in needle tip positioning, particularly relative to the costs associated with other devices and methods, and enables precise needle aspiration of radiographically detected lesions suspicious for cancer.

BRIEF DESCRIPTION OF THE DRAWINGS

FIG. 3 is a sectional view along line 3—3 at FIG. 1;

FIG. 4 is a sectional view along line 4—4 at FIG. 1;

FIG. 8 is another radiograph produced using the device of the present invention;

FIG. 9 is a cross-sectional fragmentary view of a probe positioned in accordance with the present invention; and FIG. 10 is still another radiograph produced in accordance with the present invention.

DETAILED DESCRIPTION OF THE PREFERRED EMBODIMENTS

Figure 1:
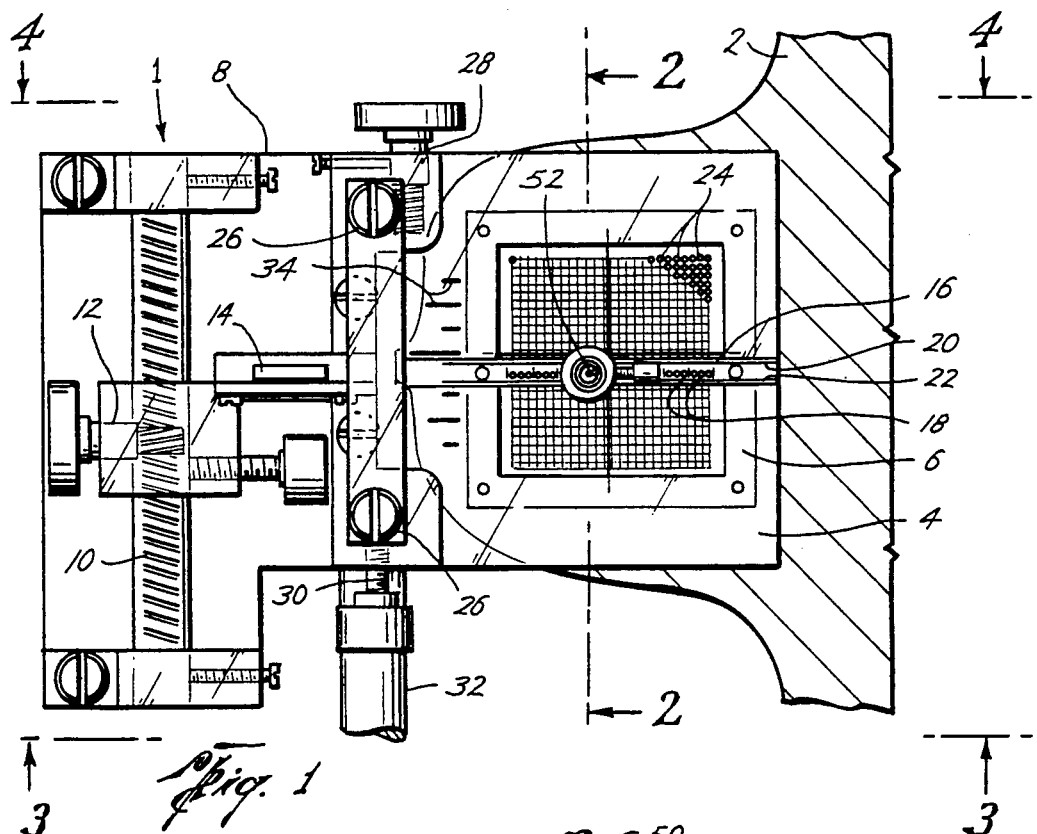
FIG. 1 is a schematic diagram of a device in accordance with the present invention.
Figure 2:
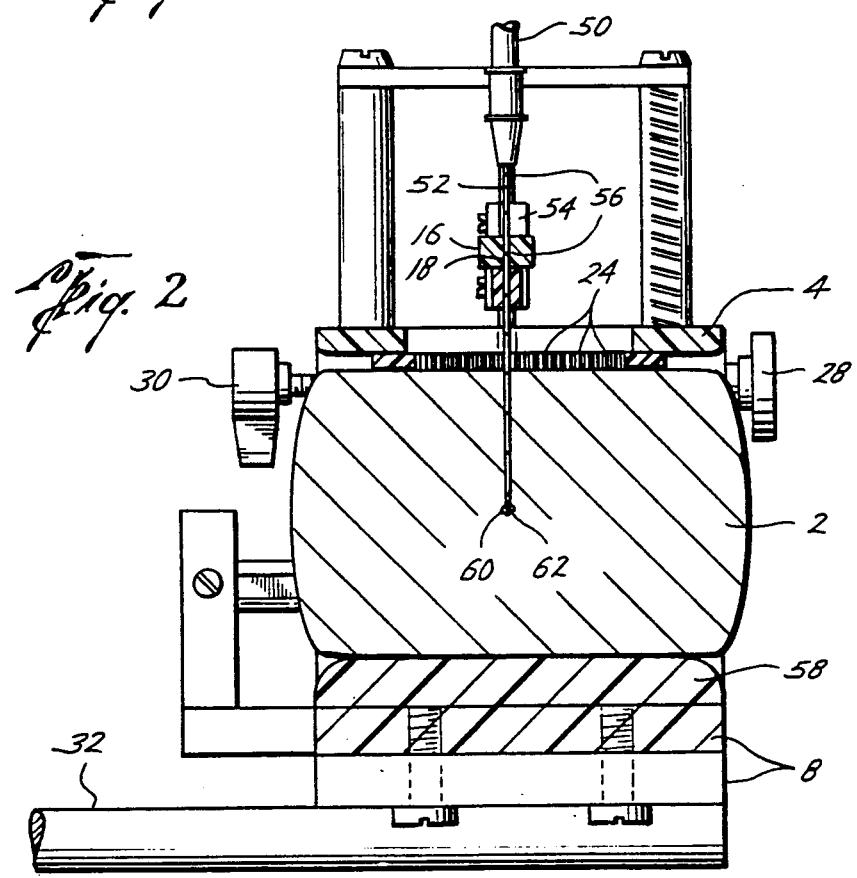
FIG. 2 is a sectional view along line 2—2 at FIG. 1.

FIGS. 1-4 illustrate a preferred embodiment of a device for precisely locating a probe in a bodily protuberance. As shown in FIGS. 1 and 2, a bodily protuberance such as breast 2 is secured and compressed between first radiolucent platform 58 and second radiolucent platform 4 of breast lesion localizer 1. Breast 2 is compressed an amount to enable creation of a radiograph of sufficient clarity to indicate the presence of lesions within breast 2. First platform 58 and second platform 4 are held in parallel and spaced relation relative to each other by second platform position adjustment support 26 which is preferably fixedly positioned relative to first platform 58 and radiolucent base 8. Second platform position adjustment 28 interengages second platform position adjustment support 26 enabling second platform 4 to be adjustably positioned relative to first platform 58. Second platform position lock 30 also interengages platform support 26 enabling breast 2 to be securely held between first platform 58 and second platform 4.

Insert 6 is positionable in second platform 4. Insert 6 comprises a plurality of insert probe passages 24. Insert passages 24 are preferably positioned in a plurality of rows and each passage 24 is sized to allow radiopaque needle probe 52 to pass with minimal excess clearance. Insert 6 is preferably removable for cleaning or replacement.

Radiolucent probe guide 16 is positionable in proximal relation to second platform 4 and in distal relation to first platform 58. Probe guide position adjustment 10 interengages probe guide position adjustment 12 enabling probe guide 16 to be positionable proximate substantially all rows of insert probe passages 24. Probe guide 16 comprises a plurality of probe guide probe passages 18 preferably positioned in a row. Probe guide passages 18 are spaced to allow probe 52 to pass through probe guide probe passages 18 and insert probe passages 24 when probe guide 16 is positioned proximate a row of insert probe passages 24.

Radiopaque probe guide markers 20,22 are fixedly positioned lengthwise relative to and along probe guide 16. Radiopaque markers 34 are fixedly positioned relative to second platform 4.

Referring to FIGS. 3-4, probe guide markers 20,22 are shown in confronting relation to radiopaque scale markers 14. As further shown in FIG. 1, in a preferred embodiment scale markers 14 are positioned coplanar to probe guide 16. Probe guide position adjustment 12 preferably simultaneously adjusts the position of probe guide 16 and scale markers 14 enabling probe guide 16 and scale markers 14 to remain in a coplanar relationship.

Radiopaque needle probe 52 is positionable through probe guide probe passages 18 and insert probe passages 24 and further positionable within breast 2. As shown in FIG. 2, with needle tip 62 of needle probe 52 positioned immediate target lesion 60, adjustable probe stop 54 enables the depth of needle 52 to be substantially fixed. Therefore, with probe stop 54 positioned flush with probe guide 16, needle 52 will not further penetrate into breast 2. Aspirator tube 50 positioned opposite needle tip 62 on needle 52 allows aspiration of cells proximate target lesion 60. Such aspirated cells may be examined by a cytopathologist or other examiner using methods known in the art to determine the nature of the aspirated cells particularly with regard to cancerous cells.

In a preferred embodiment, breast lesion localizer 1 is positioned on radiolucent base support arm 32 enabling a radiograph to be exposed through breast lesion localizer 1 onto a radiograph without support means interfering in the exposure of the radiograph.

Figure 5:
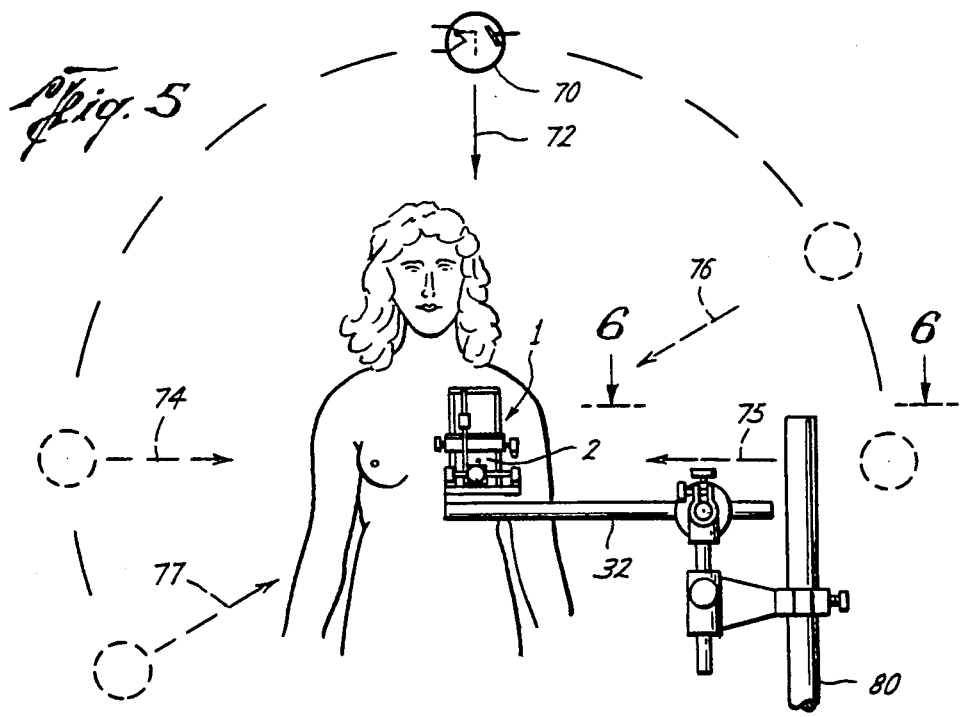
FIG. 5 is a frontal view of a patient utilizing the present invention.
Figure 6:
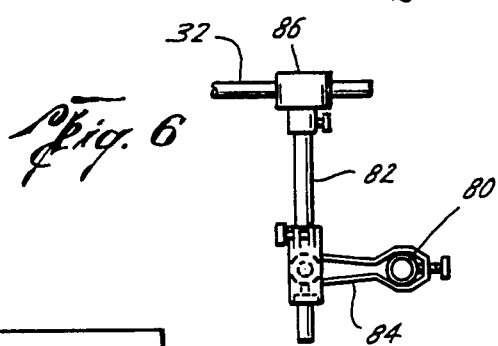
FIG. 6 is a schematic view along line 6—6 at FIG. 5.

Referring to FIGS. 5 and 6, breast lesion localizer 1 is shown with breast 2 adjustably secured between first platform 58 and second platform 4. Radiolucent support bar 32 supports breast lesion localizer 1. Radiolucent support bar 32 is adjustably secured to second support clamp 86. Second support clamp 86 is adjustably secured to intermediate support rod 82 through first support clamp 84. First support clamp 84 is adjustably secured to support rod 80. Support rod 80 is preferably attachable to base 8 to support breast lesion localizer 1 and provide minimal interference in creating radiographs with localizer 1 positioned proximate breast 2. The support system avoids the placement of radiopaque components in the path defined by second platform 4, target 60 and first platform 58 allowing a radiograph to be created substantially along this path.

In another preferred embodiment of the present invention, second platform 4 comprises a bore through second platform 4 enabling passage of needle 52 without the use of a plurality of probe passages in second platform 4.

Figure 7:
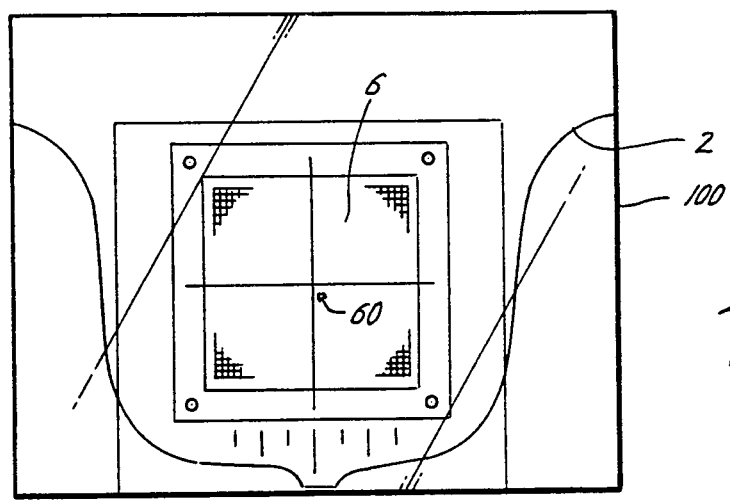
FIG. 7 is a radiograph produced using the device of the present invention.

Referring to FIGS. 5 and 7, in a preferred method of localizing a breast lesion, breast 2, containing a suspect lesion, is secured in localizer 1. First radiograph 100 is created by directing an energy beam from a radiographic beam source, such as x-ray tube 70, through second radiolucent platform 4, including radiopaque markers 34, through breast 2 and target lesion 60, through radiolucent platform 58 and radiolucent base 8 onto the x-ray sensitive surface of radiograph 100. Radiograph 100 provides two-dimensional coordinate location of target lesion 60 relative to insert 6. Preferably beam path 72 utilized to create radiograph 100 is generally perpendicular to second platform 4.

Referring further to FIGS. 1 and 8, probe guide 16 is then positioned immediate target lesion 60 within beam path 72. First-supplemental radiograph 150 is preferably created showing target lesion 60 positioned immediately beneath probe guide 16. Lengthwise positioned probe guide radiopaque markers 20 and 22 border lesion 60 in radiograph 150. As further shown in FIG. 8, probe guide probe passage 18A is positioned substantially directly above lesion 60. Thus, a probe inserted through probe guide passage 18A that is of sufficient length will pass through the immediate vicinity of target lesion 60. Radiographs 100 and 150 are created by positioning x-ray tube 70 substantially along beam path 72. Radiopaque probe 52 is preferably inserted in passage 18A and enables ready identification of passage 18A in subsequent radiographs.

Radiograph 200 is preferably produced by positioning x-ray tube 70 along beam path 74, 75, 76 or 77. Beam paths 74, 75, 76 and 77 are generally transverse to beam path 72. In a preferred embodiment, x-ray tube 70 is positioned along beam path 74, 75, 76 or 77. As additionally shown in FIG. 9, radiopaque needle probe 52 is positionable through probe guide probe passage 18A and through a corresponding insert probe passage 24.

Referring to FIGS. 4, 9 and 10, radiopaque scale markers 14 are positioned coplanar to probe guide 16 enabling radiopaque scale markers 14 to indicate the depth needle tip 62 is preferably to be inserted to reach target lesion 60. Clearly, the coplanar positioning of radiopaque markers 14 relative to lesion 60, as shown in radiograph 200, prevents a proportioning problem in radiograph 200 were the scale shown by markers 14 not coplanar with the lesion. Where a scale is not coplanar with the lesion, significant difficulties occur in determining the precise depth at which to place needle tip 62 to reach lesion 60.

Referring to FIGS. 9 and 10, needle tip 62 is positioned abutting breast 2 through probe guide passage 18A. Needle stylet 99 preferably is positioned within needle 52 to prevent undesired cells from entering needle 52 prior to positioning needle tip 62 at lesion 60.

To determine the depth to which needle 52 must be inserted, coplanar radiopaque scale 14 is examined to determine the linear distance needle tip 62 must travel to reach lesion 60. By way of example, FIG. 10 illustrates lesion 60 positioned at approximately 3.8 on coplanar scale 14. Probe guide radiopaque marker 22 is located at 9.4 on coplanar scale 14. Therefore, knowing the distance between radiopaque markers 22 and insert 6 where insert 6 secures breast 2 to be 2.4 on radiopaque scale 14, needle tip 62 must be inserted a distance (9.4–2.4)–3.8 or 3.2 marks on scale 14. As will be clear to one skilled in the art, scale 14 is used to indicate relative distance between lesion 60, probe guide 16 and second platform 4. Thus scale 14 may be fixedly positioned relative to probe guide 16, second platform 4 or other means for support which position scale 14 coplanar to probe guide 16 and substantially perpendicular to platforms 4 and 58.

In a preferred embodiment, needle probe 52 comprises markings 56 which correspond to markings 14 thus readily enabling the insertion of needle tip 62 to the calculated depth where target lesion 60 resides in breast 2.

In another preferred embodiment of the present invention, an additional radiograph may be taken along a second beam path generally transverse to beam path 72. The distance for insertion of needle tip 62 is calculated for the additional radiograph using the procedure used to calculate the insertion distance in the earlier radiograph. Needle tip 62 is then preferably inserted a distance equal to the average of the distances calculated from the radiographs produced along the beam paths generally transverse to beam path 72. By way of example, in FIG. 5, if a first radiograph is taken along beam path 72 and a second radiograph is taken along beam path 76, preferably an additional radiograph may be taken along beam path 77. By way of further example, if a first radiograph is taken along beam path 72 and a second radiograph is taken along beam path 74, preferably an additional radiograph may be taken along beam path 75.

In a preferred embodiment of the present invention, probe guide passages 18 and insert probe passages 24 comprise 1 millimeter (mm) diameter passages positioned 2 mm on center relative to each adjacent passage. Further, in a preferred embodiment, needle 52 comprises a 20-gauge needle. As will be clear to one skilled in the art, the precision of needle tip placement in accordance with the present invention is a function, inter alia, of the tolerances between the probe, the probe passages and the size of the probe and probe passages. Therefore, in the preferred embodiment comprising 1 mm holes, 2 mm on center, precision location of the needle tip is approximately plus or minus 1 mm. Greater precision is obtainable by utilizing smaller or more densely packed passages or a combination thereof in conjunction with an appropriately sized needle to pass through the passages. Further, precision may be limited by limits on needle size available for aspirating cells.

Further modifications and alternative embodiments of the methods and apparatus of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size and arrangement of parts. For example, equivalent elements or materials may be substituted for those illustrated and described herein, parts may be reversed, and certain features of the invention may be utilized independently of the use of other features, all as would be apparent to one skilled in the art after having the benefit of this description of the invention.

We claim:

1. A device for positioning a probe in a bodily protuberance comprising:
    a base;
    a first radiolucent platform attached to said base;
    a second radiolucent platform attached to said base being adjustably positionable in parallel and space relation to said first platform to secure and compress a bodily protuberance between said first and second platforms;
    a radiolucent insert positioned in said second platform, said insert comprising a plurality of probe passages, said probe passages being positioned in a plurality of rows;
    means for adjusting said spaced relation of said first and second platforms;
    a radiolucent probe guide comprising a plurality of probe guide passages,
        said probe guide passages being positioned in a row and spaced a distance substantially equal to the space between said insert passages,
        said probe guide being in proximal relation to said second platform and in distal relation to said first platform;
    means for supporting said probe guide in spaced relation to said insert;
    at least radiopaque scale markers positioned in a path substantially perpendicular to said first platform and in a plane substantially parallel to said row of probe guide passages.

2. The device of claim 1 wherein each row of said insert passages having said passages substantially symmetrically spaced relative to at least one other said row of insert passages.

3. The device of claim 1 wherein said scale markers are positioned substantially coplanar to said row of probe guide passages.

4. The device of claim 3 wherein said scale markers are fixedly positioned relative to said probe guide supporting means.

5. The device of claim 3 wherein said scale markers are fixedly positioned relative to said probe guide.

6. The device of claim 3 wherein said scale markers are variably positioned relative to said second platform.

7. The device of claim 1 wherein said scale markers comprise a plurality of substantially uniformly spaced radiopaque markers.

8. The device of claim 1 wherein said probe guide being adjustably positionable, whereby said row of probe guide passages are aligned with a row of said probe passages.

9. The device of claim 1 wherein said insert is removable.

10. The device of claim 1 further comprising an adjustable probe stop positioned flush with said probe guide and adapted to secure said probe at a desired depth through said probe guide.

11. The device of claim 1 further comprising means for supporting said base adjacent said bodily protuberance.

12. The device of claim 1, wherein said second platform comprises radiopaque marker means for horizontally positioning said probe guide.

13. A device for positioning a probe in a bodily protuberance comprising:
    a base;
    a first radiolucent platform attached to said base;
    a second radiolucent platform attached to said base being adjustably positionable in parallel and spaced relation to said first platform to secure and compress a bodily protuberance between said first and second platforms;
    a bore through said second platform;
    at least one radiopaque insert marker included in said second platform in a fixed position relative to said bore
    means for adjusting said spaced relation of said first and second platforms;
    a radiolucent probe guide comprising a plurality of probe guide passages,
        said probe guide passages being positioned in a row,
        said probe guide being adjustably positionable relative to said bore to enable accurate positioning of said probe within said protuberance by placing said probe through said probe guide and said bore,
        said probe guide being in proximal relation to said second platform and in distal relation to said first platform;
    means for supporting said probe guide in spaced relation to said second radiolucent platform, and
    at least two radiopaque scale markers positioned in a path substantially perpendicular to said first platform in a plane substantially parallel to said row of probe guide passages.

14. The device of claim 13 wherein said scale markers are positioned substantially coplanar to said row of probe guide passages.

15. The device of claim 13 wherein said scale markers comprise a plurality of uniformly spaced radiopaque markers.

16. A method of positioning a probe tip proximate to a target in a bodily protuberance comprising the steps of:
    providing a radiopaque probe having a probe tip;
    securing and compressing a bodily protuberance between a first radiolucent platform and a second radiolucent platform, said platforms being adjustably positioned in parallel and spaced relation, said second platform comprising a plurality of probe passages and further comprising at least one radiopaque marker in fixed position relative to said second platform probe passages;
    creating a first radiograph by steps comprising directing an energy beam in a first path through said second platform, said target and said first platform and onto a first beam sensitive surface;
    interposing a radiolucent probe guide in said first path, said probe guide comprising a plurality of probe passages positioned in a row to enable passage of a probe through one of said probe guide passages and through one of said second platform probe passages toward said target, said row of probe guide passages being substantially perpendicular to said first path;
    positioning the radiopaque probe in at least one of said probe guide passages, said probe being substantially aligned with said target along said first path;

creating a second radiograph by steps comprising directing an energy beam in a second path generally transverse to said first path through said target, through a plurality of radiopaque scale markers positioned substantially coplanar to said row of probe guide passages, said plurality of markers being further positioned to indicate position of said probe tip along said first path, and onto a second beam sensitive surface; and positioning said probe along said first path and further positioning said probe tip within said protuberance a distance along said first path generally equal to the distance along said first path of said target in said protuberance indicated by said plurality of radiopaque scale markers.

17. The method of claim 16 wherein said interposing step further comprises the substep of creating a first-supplemental radiograph arranged substantially along said first path through said interposed probe guide, said second platform, said target and said first platform and onto a first-supplemental beam sensitive surface to indicate a distance between said target and said probe tip, perpendicular to said first path.

18. The method of claim 16 wherein said step of creating a second radiograph further comprises the substep of creating a second-supplemental radiograph in a third path through said target, through said interposed probe guide, said second platform, and onto a second-supplemental beam sensitive surface to indicate a distance between said target and said probe tip parallel to said first path.

19. The method of claim 18 wherein said probe positioning step further comprises the substep of positioning said probe tip within said protuberance a distance along said first path substantially equal to the average of the distances along said first path of said target in said protuberance indicted by said plurality of markers shown in said second and second-supplemental radiographs.

20. A method of positioning a probe proximate to a target in a bodily protuberance comprising the steps of:

securing and compressing a bodily protuberance between a first radiolucent platform and a second radiolucent platform, said platforms being adjustably positioned in parallel and spaced relation, said second platform comprising a bore through said second platform, said second platform further comprising at least one radiopaque marker in fixed position relative to said bore;

creating a first radiograph by steps comprising directing an energy beam in a first path through said second platform, said target and said first platform and onto a first beam sensitive surface;

interposing a radiolucent probe guide in said first path, said probe guide comprising a plurality of probe passages positioned in a row to enable passage of a probe through one of said probe guide passages and through said bore toward said target, said row of probe guide passages being substantially perpendicular to said first path;

positioning the radiopaque probe in at least one of said probe guide passages, said probe being substantially aligned with said target along said first path;

creating a second radiograph by steps comprising directing an energy beam in a second path generally transverse to said first path through said target, through a plurality of radiopaque markers positioned substantially coplanar to said row of probe guide passages, said plurality of markers being further positioned to indicate position of said probe along said first path, and onto a second beam sensitive surface; and positioning said probe along said first path and further positioning said probe tip within said protuberance a distance along said first path generally equal to the distance along said first path of said target in said protuberance indicated by said plurality of radiopaque scale markers positioned along said first path.

* * * * *

UNITED STATES PATENT AND TRADEMARK OFFICE
CERTIFICATE OF CORRECTION

PATENT NO. : 5,056,523

DATED : October 15, 1991

INVENTOR(S) : Hotchkiss and Coggs

It is certified that error appears in the above-identified patent and that said Letters Patent is hereby corrected as shown below:

Claim 1, column 9, line 15, please delete "space" and substitute therefor --spaced--.

Claim 1, column 9, line 35, please insert after "least" --two--.

Claim 10, column 9, line 64, please delete "and" and substitute therefor --an--.

Claim 14, column 10, line 38, please delete "are" and substitute therefor --being--.

Claim 14, column 10, line 38, please delete "to".

Claim 19, column 11, line 41, please delete "indicted" and substitute therefor --indicated--.

Claim 20, column 12, line 2, please insert after "of:" the terms --providing a radiopaque probe having a probe tip;--.

Signed and Sealed this

Twentieth Day of April, 1993

Attest:

MICHAEL K. KIRK

Attesting Officer

Acting Commissioner of Patents and Trademarks